(12) United States Patent
Sano et al.

(10) Patent No.: US 8,680,158 B2
(45) Date of Patent: Mar. 25, 2014

(54) ANTIVIRAL AGENT

(75) Inventors: Shinsuke Sano, Chigasaki (JP); Takako Fukagawa, Odawara (JP); Hirokazu Yamada, Ichihara (JP); Chikara Masuta, Sapporo (JP); Hanako Shimura, Sapporo (JP)

(73) Assignees: Nippon Soda Co., Ltd., Tokyo (JP); Hokkaido University, Hokkaido (JP)

( * ) Notice: Subject to any disclaimer, the term of this patent is extended or adjusted under 35 U.S.C. 154(b) by 224 days.

(21) Appl. No.: 13/067,623

(22) Filed: Jun. 15, 2011

(65) Prior Publication Data
US 2012/0041072 A1 Feb. 16, 2012

Related U.S. Application Data

(63) Continuation of application No. 12/450,150, filed as application No. PCT/JP2008/000655 on Mar. 19, 2008, now abandoned.

(30) Foreign Application Priority Data

Mar. 23, 2007 (JP) ................................. 2007-077970

(51) Int. Cl.
*A01N 35/00* (2006.01)
*A61K 31/12* (2006.01)

(52) U.S. Cl.
USPC ........................................................ 514/682

(58) Field of Classification Search
USPC ........................................................ 514/682
See application file for complete search history.

(56) References Cited

U.S. PATENT DOCUMENTS 6,326,405 B1 * 12/2001 Kobayashi et al. ............ 514/690
2003/0077540 A1 * 4/2003 Kodama et al. ............. 430/270.1

FOREIGN PATENT DOCUMENTS

| DE | 10203135 A1 * | 7/2003 |
| EP | 1 018 336 A1 | 7/2000 |
| JP | A-2004-344110 | 12/2004 |
| WO | WO 2004/009779 A2 | 1/2004 |
| WO | WO 2007/005882 A2 | 1/2007 |

OTHER PUBLICATIONS

Bogdanova et al (Farmakol Toksikol. Jul.-Aug. 1970;33(4):488-96).*
Sprinson et al., "On Oxidative Decarboxylations with Periodic Acid," J. Biol. Chem., Jul. 1, 1946, 164(1):433-449.
Goto et al., "Characterization of Silencing Suppressor 2b of Cucumber Mosaic Virus Based on Examination of its Small RNA-Binding Abilities," *Plant Cell Physiol.*, 2007, pp. 1050-1060, vol. 48, No. 7, Oxford University Press.
Anandalakshmi et al., "A viral suppressor of gene silencing in plants," *Proc. Natl. Acad. Sci. USA*, Oct. 1998, pp. 13079-13084, vol. 95, The National Academy of Sciences.
Brigneti et al., "Viral pathogenicity determinants are suppressors of transgene silencing in *Nicotiana benthamiana*," *The Embo Journal*, 1998, pp. 6739-6746, vol. 17, No. 22, Oxford University Press.

(Continued)

*Primary Examiner* — Benjamin Packard
(74) *Attorney, Agent, or Firm* — Foley & Lardner LLP (57) ABSTRACT

A compound having inhibitory activity on the binding of a substance α to a PTGS suppressor protein, wherein the substance α has a property of inducing PTGS and a property of binding to the PTGS suppressor protein and shows a decrease in the property of inducing PTGS upon binding to the PTGS suppressor protein.

5 Claims, 3 Drawing Sheets

(56) References Cited

OTHER PUBLICATIONS

Voinnet et al., "A Viral Movement Protein Prevents Spread of the Gene Silencing Signal in *Nicotiana benthamiana*," *Cell*, Sep. 29, 2000, pp. 157-167, vol. 103, Cell Press.

Baulcombe et al., "Crystal structure of p19—a universal suppressor of RNA silencing," *Trends in Biochemical Sciences*, Jun. 2004, pp. 279-281, vol. 29, No. 6, Elsevier Ltd.

Qu et al., "The Coat Protein of Turnip Crinkle Virus Suppresses Posttranscriptional Gene Silencing at an Early Initiation Step," *Journal of Virology*, Jan. 2003, pp. 511-522, vol. 77, No. 1, American Society for Microbiology.

Sagan et al., "Inhibition of siRNA Binding to a p19 Viral Suppressor of RNA Silencing by Cysteine Alkylation," *Angew. Chem. Int. Ed.*, 2007, pp. 2005-2009, vol. 46, No. 12, Wiley-VCH Verlag GmbH & Co.

Matsumoto et al., "Selective Nonpeptidic Inhibitors of Herpes Simplex Virus Type 1 and Human Cytomegalovirus Proteases," *Biol. Pharm. Bull.*, 2001, pp. 236-241, vol. 24, No. 3, Pharmaceutical Society of Japan.

Lakatos et al., "Small RNA binding is a common strategy to suppress RNA silencing by several viral suppressors," *The EMBO Journal*, 2006, pp. 2768-2780, vol. 25, No. 12, European Molecular Biology Organization.

Koukiekolo et al., "Effects of pH and salt concentration on the siRNA binding activity of the RNA silencing suppressor Protein p19," *FEBS Letters*, 2007, pp. 3051-3056, vol. 581, Federation of European Biochemical Societies.

Sep. 29, 2009 International Preliminary Report on Patentability issued in International Patent Application No. PCT/JP2008/000655.

Sery et al., "The Inactivation of Herpes-Simplex Virus by Chemical Agents," *American Journal of Ophthalmic Publ.*, Jan. 1, 1961, pp. 42-57, vol. 51, Chicago, IL, USA.

Fesen et al., "Inhibitors of Human Immunodeficiency Virus Integrase," *Proc. Natl. Acad. Sci. USA*, Mar. 15, 1993, pp. 2399-2403, vol. 90, No. 6, Washington DC, USA.

Zhao et al., "A Viral Protein Suppresses siRNA-directed Interference in Tobacco Mosaic Virus Infection," *Acta Biochimica et Biophysica Sinica*, Apr. 1, 2005, pp. 248-253, vol. 37, No. 4, Malden, MA, USA.

Wagner, "Studies on the Inactivation of Influenza Virus: Comparison of the Effects of p-Benzoquinone and Various Inorganic Oxidizing Agents," *The Yale Journal of Biology and Medicine*, Jan. 1, 1951, pp. 288-298, vol. 23, USA.

Ueki et al., "Inhibition of Systemic Onset of Post-Transcriptional Gene Silencing by Non-Toxic Concentrations of Cadmium," *The Plant Journal*, Nov. 2001, pp. 283-291, vol. 28, No. 3, Stony Brook, NY, USA.

Extended European Search Report issued in European Patent Application No. 08720540.7 on Dec. 23, 2009.

Depuy et al., "Cyclopentene-3,5-dione. I. Synthesis and Properties," *J. Am. Chem. Soc.*, vol. 81, No. 18, pp. 4920-4924, Sep. 20, 1959.

\* cited by examiner

CMV-infected

Effect of compound 7
of the present invention

Healthy

Figure 3

SEQUENCE LISTING

```
<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
<223> OTHER INFORMATION: Synthetic Construct - ssRNA-sense

<400> SEQUENCE: 1
uugcucaaca guaugggcau u                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic Construct - ssRNA-antisense

<400> SEQUENCE: 2
ugcccauacu guugagcaau u                                              21

<210> SEQ ID NO 3
<211> LENGTH: 34
<212> TYPE: PRT
<213> ORGANISM: Artificial Sequence
<220> FEATURE:
<223> OTHER INFORMATION: Synthetic Construct - designed peptide based on
```

```
             amino acid sequence in dsRNA binding motif of tat

<400> SEQUENCE: 3

Arg Lys Lys Arg Arg Gln Arg Arg Pro Pro Gln Gly Ser Gln Thr
1               5                   10                  15

His Gln Val Ser Leu Ser Lys Gln Pro Thr Ser Gln Ser Arg Gly Asp
            20                  25                  30

Pro Thr
```

ANTIVIRAL AGENT

CROSS-REFERENCE TO PRIOR APPLICATION

This is a continuation of Application No. 12/450,150 filed Sep. 14, 2009, which is a National Stage Application of PCT/JP2008/000655 filed Mar. 19, 2008, and claims the benefit of Japanese Patent Application No. 2007-077970 filed Mar. 23, 2007. The entire disclosures of the prior applications are hereby incorporated by reference herein in their entirety.

TECHNICAL FIELD

The present invention relates to a PTGS suppressor protein binding inhibitor and an antiviral agent having a novel mechanism of action.

BACKGROUND ART

A very large number of pathogenic viruses have spread on earth, and their infection has caused suffering or economic losses in various organisms such as animals including humans and useful plants (e.g., crops). Examples of viral diseases caused by a pathogenic virus infection include rice dwarf disease caused by rice dwarf virus infection, tomato mosaic disease caused by tobacco mosaic virus infection, human influenza caused by influenza virus infection, human hepatitis B caused by hepatitis B virus infection, and acquired immune deficiency syndrome caused by human immunodeficiency virus (HIV) infection.

Host organisms such as plants or animals, when infected with pathogenic viruses, develop various biological defense mechanisms against the infection to inhibit the growth of the viruses or to relieve the disease symptom. One of these defense mechanisms is post-transcriptional gene silencing (hereinafter, abbreviated to PTGS). PTGS is a phenomenon induced by double-stranded RNAs (dsRNAs) of viruses or the like, wherein transcribed messenger RNAs (mRNAs) are degraded in a sequence-specific manner. PTGS is a mechanism conserved not only in higher organisms such as plants or animals but also in various other organism species from protozoans to fungi and is thought to be a particularly important defense mechanism for plants which do not have an immune system, unlike animals. Specifically, in this mechanism, PTGS-inducing dsRNAs are degraded by intracellular nuclease Dicer or an enzyme analogous thereto into short RNAs of approximately 21 to 24 bases called small interfering RNAs (siRNAs), and the siRNA is further incorporated into a nuclease complex called an RNA-induced silencing complex (RISC), which in turn cleaves mRNA homologous to the siRNA sequence, thereby inhibiting the expression of the target protein such as viruses.

It has recently been revealed that many pathogenic viruses encode, as a counter against the PTGS mechanism of host organisms, a suppressor protein that inhibits this PTGS (PTGS suppressor protein; hereinafter, abbreviated to PTGS-SP) (e.g., Patent Document 1). It has further been reported that the majority of these PTGS-SPs inhibit PTGS through the direct binding to siRNAs (e.g., Non-Patent Document 1).

PTGS-SPs expressed by plant viruses have been reported, for example, HC-Pro of viruses of the genus *Potyvirus* (see Non-Patent Document 2), 2b of viruses of the genus *Cucumovirus* (see Non-Patent Document 3), p25 of viruses of the genus *Potexvirus* (see Non-Patent Document 4), p19 of viruses of the genus *Tombusvirus* (see Non-Patent Document 5), and coat proteins of viruses of the genus *Carmovirus* (see Non-Patent Document 6).

Many attempts have been made to develop preventive or therapeutic agents for the viral diseases for reducing damages caused by the viral diseases. For example, M2 ion-channel inhibitors (e.g., amantadine) and neuraminidase inhibitors (e.g., zanamivir phosphate and oseltamivir) are known as effective therapeutic agents for influenza. These M2 ion-channel and neuraminidase inhibitors probably exert therapeutic effects on influenza by preventing the influenza viruses from growing or infecting other cells. Moreover, known effective therapeutic agents for acquired immune deficiency syndrome are broadly classified into reverse transcriptase inhibitors (e.g., azidothymidine and didanosine) and protease inhibitors (e.g., ritonavir and indinavir). Multi-drug therapy using these agents exerts remarkable effects, which drastically reduces the number of deaths in advanced countries.

However, these therapeutic agents for influenza or acquired immune deficiency syndrome are also known to have side effects, and it is believed that drug resistance viruses will inevitably appear due to the variability of the viruses. Therefore, the development of a novel antiviral agent having a different mechanism of action has been demanded. Furthermore, agents against viruses, except for some agents structurally similar to nucleic acids, are only applicable to a target viral disease. Moreover, vaccination, albeit effective, must be performed before infection and has problems such as time taken to develop antibodies or the easily variable antigenic site of viruses. Furthermore, the therapeutic agents or vaccines are only applicable to a target viral disease. Therefore, therapeutic agents for viral diseases had to be developed for each type of virus.

On the other hand, various control methods have been developed for viral diseases in plants. Examples thereof include selective breeding of resistant varieties to viral diseases, raising of virus-free plants by stem tip culture or heat treatment, inhibition of pathogenic virus infection by treatment with selected attenuated viruses, and use of plants having virus resistance imparted by transformation. Moreover, examples of the control methods using agricultural chemicals include use of a fungicide that induces the resistance of plants or an insecticide that targets insect vectors or the like for viruses.

However, the breeding of resistant varieties requires a long period, and resistant strains of viruses inevitably appear. The raising of virus-free plants by stem tip culture or the like is not perfect. The use of attenuated viruses is highly effective for viral disease control. However, attenuated viruses are difficult to stably prepare and are effective only for viruses of the same species or related species. Plant defense activators have unstable effects. Spraying large amounts of insecticide that preventively controls insect vectors for viruses may lead to environmental pollution and cannot be expected to have therapeutic effects on virus-infected plants.

On the other hand, urgency and markets for antiviral agents for viral diseases in plants are much smaller than those for antiviral agents for viral diseases in humans. Therefore, it is highly possible that the cost of developing the antiviral agents for viral diseases in plants cannot be recovered even if they are developed at cost much lower than the cost of developing the antiviral agents for viral diseases in humans, for example, anti-HIV drugs or anti-influenza drugs. In addition, the existing vaccines or antiviral agents are expected, as described above, to be effective only for the target viruses, and resistant strains of viruses inevitably appear. Therefore, the development of antiviral agents for viral diseases in plants has hardly proceeded so far.

Patent Document 1: Japanese Laid-Open Patent Application No. 2004-344110

Non-Patent Document 1: Goto K., et al., Plant Cell Physiol. 2007, 48, 1050-60

Non-Patent Document 2: Anandalakshmi R., et al., Proc. Natl. Acad. Sci. USA, 1998, 95, 13079-13084

Non-Patent Document 3: Brigneti G., et al., EMBO J., 1998, 17, 6739-6746

Non-Patent Document 4: Voinnet O., et al., Cell, 2000, 103, 157-167

Non-Patent Document 5: Baulcombe D C., et al., Trends Biochem Sci. 2004, 29, 279-81

Non-Patent Document 6: Qu F., et al., J. Virol. 2003, 77, 511-522

DISCLOSURE OF THE INVENTION

Object to be Solved by the Invention

It has been demanded to provide a control method which has a mechanism of action different from conventional one as a substitute for the existing viral disease control methods described above and is used in more practical and safer manners. Thus, an object of the present invention is to provide a viral disease control agent having a mechanism of action different from conventional one.

Means to Solve the Object

The present inventors have conducted diligent studies in consideration of the object and consequently found that a therapeutic effect of reducing damages caused by viral diseases or an effect of attenuating highly virulent viruses having strong pathogenicity is obtained without toxicity to or strong influence on applicable organisms by inhibiting the binding of PTGS-SP to siRNA such that the PTGS-SP function is inhibited. Furthermore, the present inventors have actually studied the effects of compounds that actually inhibit the functions of various PTGS-SPs. Based on these findings, the present invention has been completed.

Specifically, the present invention relates to:

[1] a PTGS suppressor protein binding inhibitor containing a compound having inhibitory activity on the binding of a substance α to a PTGS suppressor protein, wherein the substance α has a property of inducing PTGS and a property of binding to the PTGS suppressor protein and shows a decrease in the property of inducing PTGS upon binding to the PTGS suppressor protein;

[2] the PTGS suppressor protein binding inhibitor according to [1], wherein the substance α is siRNA; and

[3] the PTGS suppressor protein binding inhibitor according to [1] or [2], wherein the compound is at least one selected from the group consisting of cyclic ketone compounds represented by the following formulas (1) to (6):

Formula (1)

Formula (2)

-continued

Formula (3)

Formula (4)

Formula (5)

Formula (6)

Moreover, the present invention relates to:

[4] the PTGS suppressor protein binding inhibitor according to [1] or [2], wherein the compound is a reaction product of croconic acid with hydrogen peroxide;

[5] an antiviral agent comprising as an active ingredient a compound having inhibitory activity on the binding of a substance α to a PTGS suppressor protein, wherein the substance α has a property of inducing PTGS and a property of binding to the PTGS suppressor protein and shows a decrease in the property of inducing PTGS upon binding to the PTGS suppressor protein;

[6] the antiviral agent according to [5], wherein the substance α is siRNA; and

[7] the antiviral agent according to [5] or [6], wherein the compound is at least one selected from the group consisting of cyclic ketone compounds represented by the following formulas (1) to (6):

Formula (1)

Formula (2)

-continued Formula (3)

[structure: 1,4-benzoquinone]

Formula (4)

[structure: 2,5-dichloro-1,4-benzoquinone]

Formula (5)

[structure: 2,5-dichloro-1,4-benzoquinone isomer]

Formula (6)

[structure: 5,8-dihydroxy-1,4-naphthoquinone]

Furthermore, the present invention relates to:

[8] the antiviral agent according to [5] or [6], wherein the compound is a reaction product of croconic acid with hydrogen peroxide.

BEST MODE OF CARRYING OUT THE INVENTION

A PTGS-SP binding inhibitor of the present invention is characterized by containing a compound having inhibitory activity on the binding of PTGS-SP to a substance α (hereinafter, also referred to as a "compound according to the present invention"), wherein the substance α has a property of inducing PTGS and a property of binding to the PTGS-SP and shows a decrease in the property of inducing PTGS upon binding to the PTGS-SP. The inhibition of the binding of a substance α to PTGS-SP can restore the substance α function inhibited by PTGS-SP, i.e., the function of inducing PTGS. Therefore, the use of the compound according to the present invention can reduce the inhibitory effect of viruses on PTGS, resulting in, for example, the reduced toxicity or inhibited growth of the viruses. As a result, an antiviral effect is obtained.

(PTGS-SP Protein)

The PTGS-SP targeted by the PTGS-SP binding inhibitor according to the present invention is not particularly limited as long as it is a protein that is derived from any kind of virus and has the ability to inhibit the PTGS of one or more organisms. Preferable examples of the organisms can include plants and animals. The plants can be exemplified more preferably by: food crops such as cereals (e.g., rice, wheat, and corn), pulse crops (e.g., soybean and peanut), tubers (e.g., potato and sweet potato), vegetables (e.g., Japanese radish, carrot, cabbage, lettuce, eggplant, cucumber, and tomato), and fruit trees (e.g., apple, pear, and citrus); and nonfood crops such as flowers and ornamental plants (e.g., rose, carnation, and chrysanthemum), foliage plants (e.g., ivy and maidenhair), and trees (e.g., pine and cherry). More preferable examples of the animals can include birds and mammals such as human, monkey, chimpanzee, cow, horse, pig, sheep, rabbit, dog, cat, rat, mouse, and guinea pig.

Specifically, the PTGS-SP targeted by the PTGS-SP binding inhibitor according to the present invention can be exemplified preferably by: PTGS-SPs derived from viruses whose natural host is a plant, such as HC-Pro of viruses of the genus *Potyvirus* (e.g., TuMV: turnip mosaic virus), 2b of viruses of the genus *Cucumovirus* (e.g., CMV: cucumber mosaic virus), p25 of viruses of the genus *Potexvirus* (e.g., PVX: potato virus X), p19 of viruses of the genus *Tombusvirus* (e.g., TBSV: tomato bushy stunt virus), and coat proteins of viruses of the genus *Carmovirus* (e.g., CarMV: carnation mottle virus); and PTGS-SPs derived from viruses whose natural host is an animal (particularly, a mammal), such as tat (Genbank Accession No. NC_001802 or NC_001722) of viruses of the genus *Lentivirus* (e.g., HIV: human immunodeficiency virus), NS1 (Genbank Accession No. NC_002020) of viruses of the genus *Influenzavirus A* (e.g., FLUAV: influenza A virus), NS1 (Genbank Accession No. NC_002211) of viruses of the genus *Influenzavirus B* (e.g., FLUBV: influenza B virus), and NS1 of viruses of the genus *Influenzavirus C* (e.g., FLUCV: influenza C virus).

In addition to the above-exemplified PTGS-SPs known in the art, any protein that functions as PTGS-SP can be targeted by the PTGS-SP binding inhibitor of the present invention.

Whether a certain protein is a PTGS-SP can be confirmed by: for example, artificially inducing PTGS of an arbitrary gene in a cell; causing the cell to express the protein simultaneously with a protein encoded by the arbitrary gene; and examining the recovery of the arbitrary gene from PTGS, compared with the cell not expressing the protein. The decrease in PTGS can be confirmed by detecting a decrease in the accumulation level of mRNAs of the gene targeted by PTGS or a decrease in the accumulation level of its target protein itself.

For example, whether a certain protein is a PTGS-SP can be confirmed by an agroinfiltration method which involves: injecting a GFP (green fluorescence protein) gene into the intercellular space of a plant leaf using *Agrobacterium*; and transiently inducing PTGS of the GFP gene. A virus gene encoding a PTGS-SP candidate is expressed simultaneously with the GFP gene, and the protein encoded by this virus gene is identified as PTGS-SP when light emitted by GFP is observed. Alternatively, it can also be confirmed by a protoplast method which involves transiently inducing PTGS of the GFP gene using the protoplast of a plant leaf. In this case, the GFP gene and so on are directly incorporated into the protoplast by polyethylene glycol (PEG), and PTGS-SP can be identified based on the presence or absence of light emitted by GFP.

(Substance α)

The substance α according to the present invention is not particularly limited as long as it is a substance that has property of binding to any PTGS-SP and property of inducing PTGS in the cell of any organism and shows a decrease in its own property of inducing PTGS upon binding to the PTGS-SP. The substance α is preferably a nucleic acid, more preferably virus-derived RNA (e.g., dsRNA or siRNA), and even more preferably siRNA. Specifically, the RNA used as the substance α can be exemplified by a virus-derived RNA sequence or a portion thereof and can be exemplified more preferably by virus-derived siRNA of 21 to 23 bases.

The sequence of the dsRNA or siRNA used as the substance α according to the present invention is not particularly limited and is preferably a sequence (or a partial sequence thereof) corresponding to the nucleic acid of a virus serving as a target to obtain the antiviral effect or an RNA sequence transcribed from the nucleic acid, more preferably a sequence of 20 to 27 bases corresponding to the nucleic acid of a virus serving as a target to obtain the antiviral effect or an RNA sequence transcribed from the nucleic acid, and even more preferably a sequence of 21 to 23 bases corresponding to the nucleic acid of a virus serving as a target to obtain the antiviral effect or an RNA sequence transcribed from the nucleic acid.

Whether the substance α such as dsRNA or siRNA binds to PTGS-SP can be confirmed by using a method described later such as surface plasmon resonance, single-molecule fluorescence analysis, gel shift assay, and thermal denaturation. Moreover, whether the substance α such as dsRNA or siRNA shows a decrease in its property of inducing PTGS upon binding to the PTGS-SP can be confirmed by: artificially inducing PTGS of an arbitrary gene in a cell; causing the cell to express PTGS-SP; and examining the promotion of the intracellular PTGS in the presence of the particular substance, compared with the absence of the substance.

(Inhibitor of the Present Invention)

The compound used as the inhibitor according to the present invention is not particularly limited as long as it has inhibitory activity on the binding of a substance α to PTGS-SP. The compound according to the present invention also includes compounds such as proteins (e.g., antibodies) and nucleic acids. Specifically, the compound according to the present invention can be exemplified preferably by compounds shown in Table 1 below or derivatives thereof.

These compounds are cyclic ketone compounds. The compounds of compound Nos. 7 and 8 are reaction products of croconic acid with hydrogen peroxide, synthesized in Synthesis Examples 1 and 2, respectively. The compound according to the present invention other than the compounds shown in Table 1 can be identified easily by screening using an evaluation system of the present invention (in vitro and in vivo screening methods) described later.

TABLE 1

| Compound No. | Structural formula |
|---|---|
| 1 |  |
| 2 |  |
| 3 |  |
| 4 |  |
| 5 |  |
| 6 |  |
| 7 | Compound of Synthesis Example 1 |
| 8 | Compound of Synthesis Example 2 |
| 9 |  |
| 10 |  |
| 11 |  |
| 12 |  |

TABLE 1-continued

| Compound No. | Structural formula |
|---|---|
| 13 | 2,6-dichloro-1,4-benzoquinone |
| 14 | 2,5-dichloro-1,4-benzoquinone |
| 15 | 2,5-dihydroxy-1,4-benzoquinone |
| 16 | 2,3-dimethoxy-5-methyl-1,4-benzoquinone |
| 17 | tetrahydroxy-1,4-benzoquinone, 2Na⁺ salt |
| 18 | 3-amino-2-cyclohexen-1-one |
| 19 | 3-hydroxy-2-methyl-4H-pyran-4-one |
| 20 | 5,8-dihydroxy-1,4-naphthoquinone |

Of these compounds, the compounds of compound Nos. 5, 6, 7, 8, 12, 13, 14, and 20 are preferred.

Of the compounds of above Table 1, compound Nos. 7 and 8 are novel compounds, and the compounds other than compound Nos. 7 and 8 are commercially available.

These compounds or derivatives thereof can be synthesized by performing a reaction known in the art with appropriate compounds as raw material compounds. Particularly, the above compound Nos. 7 and 8 can be synthesized by, for example, methods specifically described later in Examples.

The PTGS-SP binding inhibitor of the present invention may contain only one of the compounds according to the present invention or may contain two or more thereof.

(Antiviral Agent of the Present Invention)

An antiviral agent of the present invention is characterized by comprising the compound of the present invention as an active ingredient. The use of the antiviral agent of the present invention can restore the substance α function inhibited by PTGS-SP, i.e., the function of inducing PTGS. Based on such a mechanism of action, the antiviral agent of the present invention can reduce the inhibition of PTGS caused by highly virulent viruses, resulting in, for example, the inhibited growth or reduced toxicity of the viruses. As a result, the antiviral agent of the present invention exerts an antiviral effect.

The antiviral agent of the present invention may contain only one of the compounds according to the present invention as an active ingredient or may contain two or more thereof as active ingredients. Moreover, it is preferred from the viewpoint of obtaining a more excellent antiviral agent that the antiviral agent of the present invention should further contain a substance that promotes the general resistance of organisms to viruses unless the PTGS-SP binding inhibitory activity of the compound according to the present invention is inhibited. The substance that promotes the resistance of host organisms to viruses is not particularly limited and can be exemplified preferably by substances that promote the resistance of plants to viruses, such as fungicides known as plant defense activators (e.g., probenazole and tiadinil), or isonicotinic acid, salicylic acid, and ascorbic acid).

The antiviral agent of the present invention may contain optional additional ingredients unless the PTGS-SP binding inhibitory activity of the compound according to the present invention is inhibited. The optional additional ingredients can be exemplified by diluents or excipients such as fillers, expanders, binders, wetting agents, disintegrants, surfactants, and lubricants.

The dosage form of the PTGS-SP binding inhibitor or the antiviral agent of the present invention is not particularly limited and can be selected appropriately from tablets, pills, powders, solutions, suspensions, emulsions, granules, capsules, suppositories, injections (solutions, suspensions, etc.), ointments, inhalants, sprays, and so on according to an applicable organism used. The amount of the PTGS-SP binding inhibitor or the antiviral agent used differs depending on the mode of use, an applicable organism used, the type of the compound of the present invention contained therein, and so on and can however be determined appropriately by those skilled in the art.

A method for using the PTGS-SP binding inhibitor or the antiviral agent of the present invention is not particularly limited and can be determined appropriately by those skilled in the art according to the property of the compound of the present invention contained therein, the type of an applicable organism used, and so on. When the applicable organism used is an animal, the use method can be exemplified preferably by oral administration, intravenous injection, intramuscular injection, transvaginal administration, transdermal application, and inhalation. When the applicable organism used is a 
plant, the use method can be exemplified preferably by foliage application, dip treatment, injection into soil, seed disinfection, and smoking.

The amount of the PTGS-SP binding inhibitor or the antiviral agent of the present invention used is not particularly limited and can be determined appropriately by those skilled in the art according to the type of an applicable organism used, a use method, and so on. Particularly, when the applicable organism used is an animal, the amount can be selected appropriately according to the age, body weight, and condition of the applicable organism used, an administration method, and so on.

(Screening Method)

1) In Vitro Screening Method

An in vitro screening method for the compound according to the present invention is not particularly limited as long as it is an evaluation method using the degree of inhibition of the binding of a substance α to PTGS-SP as an index or an evaluation method which involves measuring the specific binding to PTGS-SP. Whether or not a test compound inhibits the binding of a substance α to PTGS-SP or the degree of inhibition of the binding can be measured quantitatively and evaluated by using, for example, a known method such as single-molecule fluorescence analysis, surface plasmon resonance, gel shift assay, dual polarization interferometry, photothermal spectroscopy, and quartz crystal microbalance. The single-molecule fluorescence analysis method eliminates the need of sample immobilization and achieves multi-sample treatment under conditions of a solution system close to an in vivo environment. However, this method has the disadvantage that it is susceptible to interference of the autofluorescence of a compound. The surface plasmon resonance method requires sample immobilization and is however not influenced by the autofluorescence of a compound. The gel shift assay method is unsuitable for multi-sample treatment and however has the advantage that it eliminates the need of sample immobilization and is not influenced by the autofluorescence of a compound.

The single-molecule fluorescence analysis method is an approach which involves: detecting a change in the behavior of labeled fluorescent molecules by measuring the number, intensity, or the like of the labeled fluorescent molecules using a confocal laser scanning microscope: and analyzing the intermolecular interaction between two substances. Screening based on the single-molecule fluorescence analysis method can be performed, for example, by applying a sample solution comprising PTGS-SP, a fluorescently labeled substance α, and a test compound to a measurement apparatus for single-molecule fluorescence analysis such as Olympus MF20 to detect a change in the behavior of the labeled substance α.

The surface plasmon resonance method is an apparatus which involves: monitoring a change in refractive index caused by, for example, a change in the weight of molecules immobilized on a thin gold film; and analyzing the intermolecular interaction between two substances. Screening based on the surface plasmon resonance method can be performed, for example, by: immobilizing a substance α onto sensor chip surface; and applying a sample solution comprising PTGS-SP and a test compound to a Biacore measurement apparatus or the like to detect, as a change in the refractive index of the solution, a change in the weight of molecules caused by the binding of the substance α immobilized on the sensor chip to the PTGS-SP.

The gel shift assay method is an approach which involves: mixing two high molecular substances; subjecting the mixture to electrophoresis; and analyzing whether the two substances are bound with each other, from the electrophoretic band positions or concentrations. Screening based on the gel shift assay can be performed, for example, by subjecting a sample solution comprising a labeled substance α, PTGS-SP, and a test compound to polyacrylamide gel electrophoresis using a universal apparatus. The binding of the substance α to the PTGS-SP increases a molecular weight, resulting in slow migration. By contrast, when the binding of the substance α to the PTGS-SP is inhibited by the compound, the migration of the substance α is faster. Therefore, the degree of the binding can be analyzed by comparing these electrophoretic band positions or amounts.

2) In Vivo Screening Method

An in vivo screening method for the compound according to the present invention is not particularly limited as long as it is an evaluation method using the degree of inhibition of the PTGS-SP function as an index. Whether or not a test compound inhibits the PTGS-SP function can be evaluated by, for example, an agroinfiltration method, a protoplast method, a silencing plant method using a change in flower color as an index, or a symptom test method which involves examining the symptom of a viral disease using plant seedlings.

The agroinfiltration method is a method which involves: simultaneously injecting, for example, a GFP gene and a viral PTGS-SP gene into the intercellular space of a plant leaf using *Agrobacterium* for transient transformation; and conducting evaluation based on the principle that the GFP fluorescence disappears when PTGS functions while the GFP fluorescence is observed when the viral PTGS-SP functions. Furthermore, by treating the plant leaf with a test compound before and after the gene injection, the test compound can be determined to inhibit the PTGS-SP function when the GFP fluorescence disappears.

The protoplast method is a method based on the same principle as that of the agroinfiltration method. Specifically, this method utilizes protoplast instead of the plant leaf and involves: directly incorporating a firefly luciferase gene and a viral PTGS-SP gene into the protoplast by use of polyethylene glycol; and conducting evaluation based on the principle that light emission derived from the luciferase activity disappears when PTGS functions while stronger light emission is observed when the viral PTGS-SP functions. By treating the protoplast with a test compound, the test compound can be determined to inhibit the PTGS-SP function when light emission derived from the luciferase activity is significantly decreased, compared with untreated protoplast.

The silencing plant method is a method which utilizes the principle that a variety whose flower color is wholly or partially white shows a change in the flower color when infected with a plant virus having PTGS-SP. Specifically, this method utilizes the fact that the expression of pigment genes is inhibited by natural PTGS in many white flowers. The inhibition of pigment expression by PTGS is canceled by the virus infection such that the pigment gene is expressed. As a result, the flower exhibits a red or blue color changed from the white color. Here, the flower is treated with a compound, and the inhibitory effect of the compound can be determined based on a white flower color recovered by the inhibition of the viral PTGS-SP function.

The symptom test method using plant seedlings is a method which involves observing the symptom of a viral disease to determine the antiviral effect of a compound. Specifically, in this method, the plant seedlings are treated with a compound before and after inoculation of a plant virus whose infection causes a severe symptom in the plants, and the antiviral effect is determined based on the severity of the symptom.

3) Methods for Preparing PTGS-SP and Substance α for Screening

The PTGS-SP targeted by the PTGS-SP binding inhibitor according to the present invention can be obtained using a universal approach, for example, PCR based on sequence information of the GenBank Accession No. described above.

The PTGS-SP can be expressed in, for example, an expression system using *E. coli*, yeast, or insect cells or a cell-free protein synthesis system derived from wheat germs or rabbit reticulocytes.

When *E. coli* is used, a tag sequence is added to a sequence encoding the PTGS-SP of interest, and the sequence is inserted into an arbitrary vector for *E. coli* expression, with which an arbitrary *E. coli* strain can then be transformed to express the PTGS-SP. Then, it is preferred that the PTGS-SP is purified according to a standard method based on the type of the added tag. The PTGS-SP can be purified easily by adding, for example, His-tag for TBSV p19; or MBP (maltose-binding protein) for TAV (tomato aspermy virus) 2b (TAV 2b) or HIV tat, and can be used without troubles in the evaluation system.

In the present invention, instead of the PTGS-SP, a synthetic peptide having a partial structure thereof can also be used in the evaluation system. The synthetic peptide can be obtained as a peptide of 20 to 40 bases comprising the portion of two or more primarily consecutive or adjacent strongly basic amino acids (arginines or lysines) using a usual approach, for example, solid-phase synthesis using an Fmoc or Boc method based on the sequence information of the PTGS-SP.

In the present invention, instead of the PTGS-SP, even a length or sequence variant of a synthetic peptide having a partial structure thereof can also be used in the evaluation system of siRNA binding inhibition. The variant peptide used in the siRNA binding test must have a sequence of three or more primarily consecutive or adjacent strongly basic amino acids (arginines or lysines). For example, for HIV tat, consecutive arginines or lysines starting at N-terminal position 49 are important, and its ability to bind to siRNA is decreased by converting even one of arginines 52, 53, and 55 to a neutral amino acid leucine and the ability is lost by converting two or more thereof to leucine. The ability to bind to siRNA is maintained even if all of these arginines are converted to another strongly basic amino acid lysine. On the other hand, the ability to bind to siRNA is maintained even if independently located arginine such as arginine 78 is converted to a neutral amino acid leucine.

Moreover, the nucleic acid as the substance α, such as dsRNA or siRNA, can be obtained using a universal approach, for example, PCR.

EXAMPLES

Hereinafter, the present invention will be described more specifically with reference to Examples. However, the technical scope of the present invention is not intended to be limited to these Examples.

(Synthesis of Compound)

Synthesis Example 1

Preparation of Compound 7

3.0 g of croconic acid was dissolved in 30 ml of pure water. To the solution, 1.2 g of a 30% hydrogen peroxide solution was added at room temperature, and the reaction solution was stirred at 20 to 30° C. for 3 days. The reaction solution was concentrated under reduced pressure to obtain 2.6 g of a compound 7. $^{13C}$-NMR (D$_2$O) δ178.6, 129.5, 75.7.

Synthesis Example 2

Preparation of Compound 8

5.0 g of croconic acid was dissolved in 50 ml of pure water. To the solution, 2.0 g of a 30% hydrogen peroxide solution was added at room temperature, and the reaction solution was stirred at 100° C. for 24 hours. The reaction solution was concentrated under reduced pressure to obtain 3.3 g of a compound 8. $^{13C}$-NMR (D$_2$O) δ 195.3, 193.9, 180.5, 178.7, 176.7, 161.7, 151.3, 150.0, 129.7, 75.8, 73.1, 72.5, 59.9, 45.9, 39.8.

(Compound Screening)

1. Preparation of Biotinylated siRNA

Single-stranded RNA (sense strand: SEQ ID NO: 1) consisting of 21 bases was prepared, and this sequence was 3'-terminally biotinylated. Next, single-stranded RNA (antisense strand: SEQ ID NO: 2) consisting of 21 bases complementary to this sense strand was annealed thereto. This annealing product was purified to prepare biotinylated siRNA of 21 base pairs.

2 Preparation of PTGS-SP

1) Preparation of TBSV-p19

The PTGS-SP p19 (Genbank Accession No. NC_001554) of TBSV used in screening was expressed and purified as follows: constructs comprising a p19 gene and a flag-tag sequence ligated to a vector pCold I DNA (TAKARA BIO INC.) for cold shock expression were prepared, and *E. coli* BL21 strains were transformed with the constructs. The strains were cultured at 15° C. for 24 hours in the presence of 0.1 mM IPTG to induce the expression. The strains were collected and homogenized. After centrifugation, the supernatant was subjected to extraction using a vector-derived His-tag and an Ni-NTA column with 200 mM to 500 mM imidazole. The expressed p19 was confirmed using anti-flag antibodies. The p19 in the extraction fraction was purified.

2) Preparation of TAV-2b

The 2b (Genbank Accession No. NC_003838) of TAV used in screening was expressed and purified as follows: constructs pMAL-TAV2b-flag comprising a TAV-2b gene and a flag-tag sequence ligated to a vector pMAL-c2X (BioLabs Inc.) were prepared, and *E. coli* strains JM109 were transformed with the constructs and cultured in an LB/Amp medium at 37° C. The expression was induced for 2 hours in the presence of 0.3 mM IPTG. After centrifugation, the strains were washed and resuspended in a buffer solution. These strains were homogenized using a homogenizer. After centrifugation, the supernatant fraction was applied to an amylose-lysine column, and elution with 10 mM maltose was performed to obtain MBP-fused TAV-2b. The expressed MBP-TAV2b-flag was confirmed by SDS-PAGE and then cleaved using Factor Xa to separate between MBP and TAV2b-flag. The TAV2b-flag fraction was obtained by purification using a flag column.

3) Preparation of Synthetic Peptide

A peptide (SEQ ID NO: 3) comprising the portion of a few consecutive or adjacent strongly basic amino acids (arginines) contained in HIV tat was designed as a synthetic peptide having a partial structure of the PTGS-SP based on the sequence information of the PTGS-SP. The actual synthesis was conducted by a contract manufacturer of peptide synthesis (Biologica Co., Ltd.) to obtain a peptide having 98% purity.

3 Screening

1) Surface Plasmon Resonance Method

An apparatus Biacore X (manufactured by Biacore) was used. A solution of the 3'-terminally biotinylated siRNA (10 μg/ml) of 21 base pairs was injected at a rate of 5 μl/min to a sensor chip SA modified with streptavidin to immobilize the siRNA on the sensor chip. A test compound used in screening was dissolved in dimethylformamide (DMF) or water such that it was adjusted to 25 ppm in terms of the final compound concentration. The PTGS-SP p19 or TAV-2b wad dissolved in a buffer solution for Biacore (0.01 M HEPES, pH 7.4, 0.15 M NaCl, 3 mM EDTA) such that it was adjusted to approximately 10 μg/ml in terms of the final concentration. The test compound was mixed with the PTGS-SP. After centrifugation, bovine serum albumin was added to the supernatant, and the mixture was dialyzed at 4° C. for 2 hours using a dialysis membrane (manufactured by PIERCE, 7000MWCO) and then adjusted to the concentrations described above to obtain a sample solution of the test compound. The Biacore X apparatus was operated according to the manual to measure the influence of the test compound on the binding of the siRNA immobilized on the sensor chip to the PTGS-SP. The binding inhibition rate of the test compound was calculated with non-biotinylated free siRNA (final concentration: 0.1 μM) as a positive control when an inhibition rate obtained without the compound addition is defined as 0% and an inhibition rate obtained using the positive control is defined as 100%. The binding inhibitory activity of the compound of the present invention on the p19 or TAV-2b is shown in Table 2.

2) Gel Shift Assay Method

A test compound used in screening was dissolved in dimethylformamide (DMF) or water such that it was adjusted to 100 ppm in terms of the final compound concentration. A gel shift assay kit (LightShift Chemiluminescent EMSA Kit manufactured by Pierce) was used. The synthetic peptide of tat (500 nM) and the test compound solution were mixed into a buffer solution supplemented with 0.005% BSA, and the mixture was shaken at 25° C. for 30 minutes. Then, the biotinylated siRNA (500 pM) was mixed therewith, and the mixture was further shaken at 25° C. for 30 minutes. Each sample was electrophoresed on a 5% polyacrylamide gel and then transferred to a nylon membrane for 1 hour. The membrane was blocked and then treated with peroxidase-conjugated streptavidin. A luminol-peroxide substrate solution was added thereto for reaction, and the membrane was covered with an X-ray film and exposed to light for approximately 2 minutes. The binding inhibition rate of the test compound was calculated from the band positions and concentrations of the electrophoresed free biotinylated siRNA or the electrophoresed biotinylated siRNA bound with the synthetic peptide. The binding inhibitory activity of the compound of the present invention on the synthetic peptide of tat is shown in Table 2.

TABLE 2

| Compound No. | Structural formula | Biacore p19 25 ppm | Biacore TAV2b 25 ppm | Gel shift tat 100 ppm |
|---|---|---|---|---|
| 1 | | 80 | 80 | 10 |
| 2 | | 75 | 0 | — |
| 3 | | 0 | 90 | — |
| 4 | | 20 | 90 | — |
| 5 | | 100 | 100 | 100 |
| 6 | | 100 | 100 | 100 |
| 7 | Compound of Synthesis Example 1 | 100 | 100 | 100 |
| 8 | Compound of Synthesis Example 2 | 100 | 100 | 100 |
| 9 | | 95 | 0 | 0 |
| 10 | | 70 | 50 | — |
| 11 | | 70 | 20 | — |

TABLE 2-continued

| Compound No. | Structural formula | Biacore p19 25 ppm | Biacore TAV2b 25 ppm | Gel shift tat 100 ppm |
|---|---|---|---|---|
| 12 | (1,4-benzoquinone) | 100 | 95 | 100 |
| 13 | 2,6-dichloro-1,4-benzoquinone | — | — | 100 |
| 14 | 2,5-dichloro-1,4-benzoquinone | — | — | 100 |
| 15 | 2,5-dihydroxy-1,4-benzoquinone | 95 | 100 | 80 |
| 16 | 2,3-dimethoxy-5-methyl-1,4-benzoquinone | 80 | 0 | 0 |
| 17 | disodium salt of tetraoxocyclohexene diolate | 100 | 90 | — |
| 18 | 3-amino-2-cyclohexen-1-one | 90 | 80 | 0 |
| 19 | 3-hydroxy-2-methyl-4H-pyran-4-one | 90 | 50 | 0 |
| 20 | 5,8-dihydroxy-1,4-naphthoquinone | 100 | 80 | 100 |

3) Protoplast method

The leaf abaxial epidermis of tobacco (*Nicotiana benthamiana*) seedlings was stripped off and left standing at 25° C. for approximately 6 hours in an enzyme solution (2% cellulase RS, 0.5% macerozyme R10, 0.5 M mannitol). This solution was subjected to filtration through two-piece gauze, and mannitol (0.4 M) addition and centrifugation (300 rpm, 2 min) were repeated three times to obtain protoplast. This protoplast was transfected by a PEG method with the following four nucleic acids: an expression plasmid for firefly luciferase (Fluc) as a reporter gene, an expression plasmid for *Renilla luciferase* (Rluc) as an internal standard, dsRNA of firefly luciferase (Fluc) for inducing silencing, and a PTGS-SP CMV 2b gene. The protoplast was cultured for approximately 24 hours and then homogenized. The expression level of each Fluc or Rluc protein intracellularly expressed was measured as light emission. A test compound was added at the predetermined concentration before the culture, and its inhibitory activity was determined based on the Fluc/Rluc ratio in the presence or absence of the compound.

Figure 1:
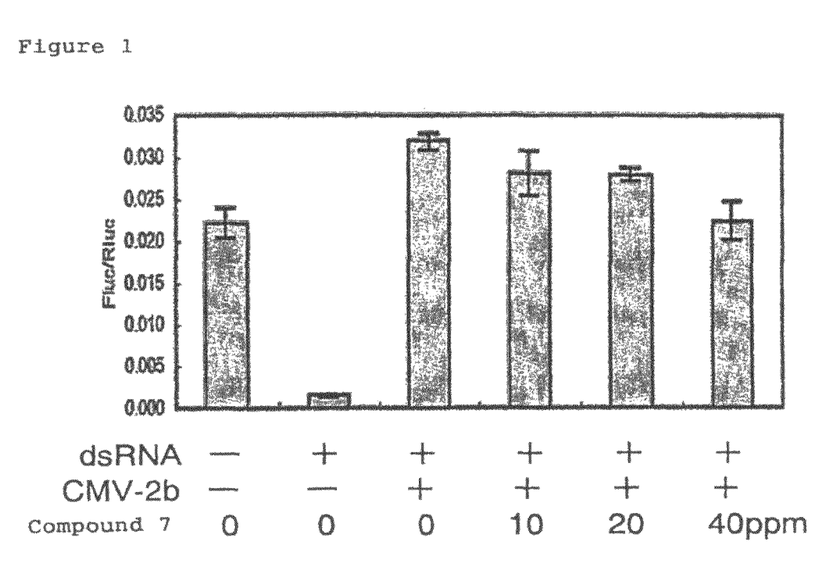
FIG. 1 It is a graph showing the inhibitory activity of compound 7 of the present invention on CMV 2b according to a protoplast method.

The inhibitory activity of the compound 7 of the present invention on the CMV-2b is shown in FIG. 1. The ordinate represents the emission intensity of the firefly luciferase reporter gene. The emission intensity was decreased in a manner dependent on the concentration of the compound 7.

4) Silencing Plant Method

A petunia variety was used whose pigment gene expression was inhibited by natural PTGS such that the flower had a white star pattern. This petunia was inoculated and infected with a CMV-L line to prepare a virus disease-affected petunia with completely inhibited natural PTGS, which was then used as a test plant for the PTGS-SP function. To eliminate individual difference, the number of the disease-affected petunia was increased by cuttings, which were then used in the inhibition test. A test compound used in screening was dissolved in dimethylformamide (DMF) or water and adjusted with an MES buffer solution to pH of 5.5 to 6.0 (final concentration: 100 to 1000 ppm). The solution of the compound of the present invention was injected into soil around the test plant, and a change in the flower color of the petunia starting to flower after 1 to 2 weeks was observed to determine the inhibitory activity of the compound on the PTGS-SP function, based on the recovery of the white star pattern.

Figure 2:
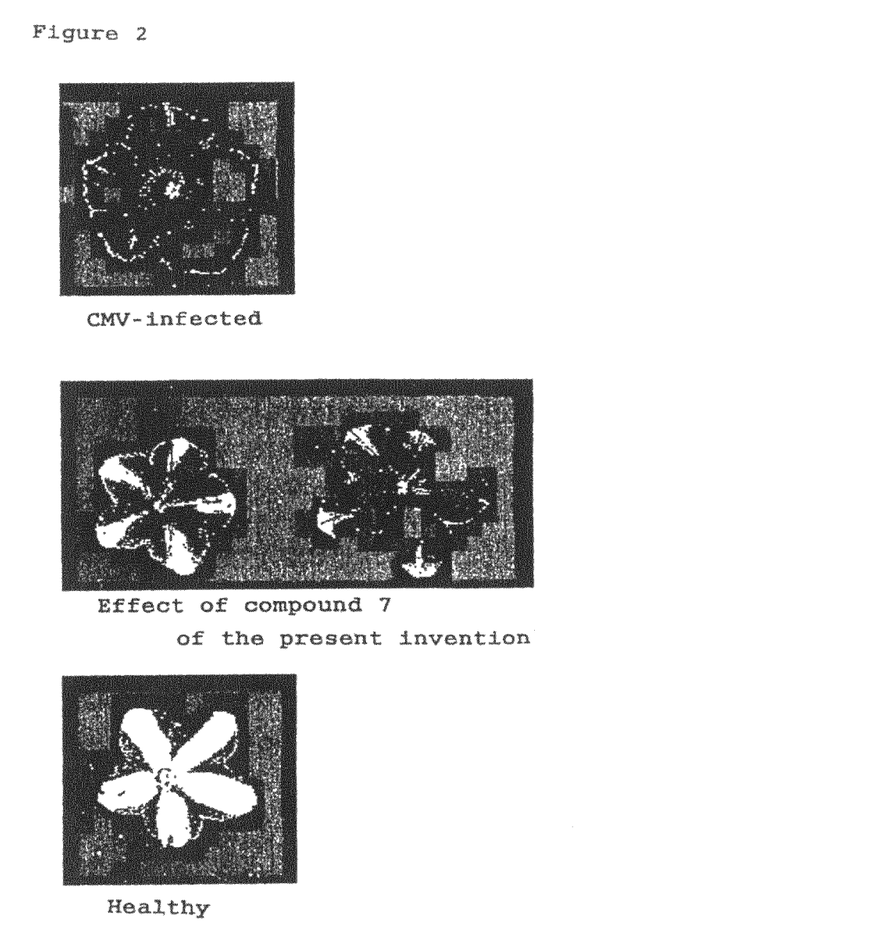
FIG. 2 It is a photograph showing the inhibitory activity of compound 7 of the present invention on CMV 2b according to a silencing plant method.

The inhibitory activity of the compound 7 of the present invention on the CMV-2b is shown in FIG. 2.

The CMV-infected petunia flower (upper box of FIG. 2) had no detectable white star pattern, whereas the flower underwent the injection of the compound 7 of the present invention into soil (middle box of FIG. 2) recovered a white star pattern as in a healthy flower (lower box of FIG. 2).

5) Symptom Test Method

A compound solution diluted to the predetermined concentration was gently injected with a syringe into the abaxial leaf epidermis of tobacco (*Nicotiana benthamiana*) seedlings. A dry leaf infected with a virus (TAV) was ground with a 10-fold volume of a 0.1 M phosphate buffer solution (pH 7.0) to prepare a crude sap, which was then used as an inoculation sap and wound-applied using Carborundum to the surface of the tobacco leaf to which the compound was injected. After the inoculation, the symptom of the viral disease was observed to determine the antiviral activity of the compound.

Figure 3:
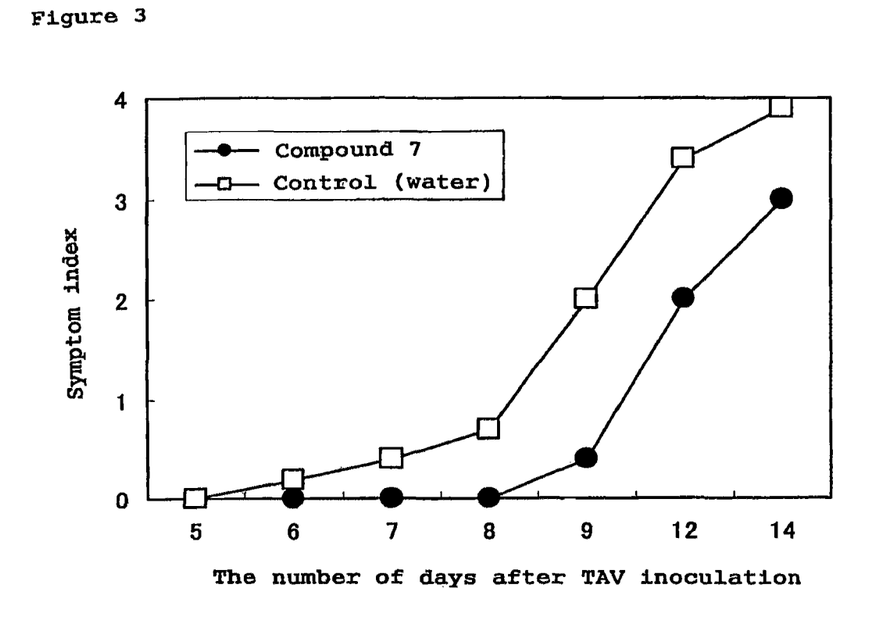
FIG. 3 It is a graph showing the antiviral activity of compound 7 of the present invention according to a symptom test method.

The antiviral activity of the compound 7 of the present invention is shown in FIG. 3. The progression of the symptom in the tobacco treated with the compound 7 of the present invention was slower than that in untreated tobacco, demonstrating the inhibition of pathogenesis.

INDUSTRIAL APPLICABILITY

A PTGS-SP binding inhibitor of the present invention can inhibit the binding of PTGS-SP produced by a virus to a substance α such that the PTGS-SP function is decreased, wherein the substance α has the property of inducing PTGS and the property of binding to the PTGS-SP and shows a decrease in the property of inducing PTGS upon binding to the PTGS-SP. The PTGS-SP binding inhibitor of the present invention can decrease the PTGS inhibitory effect involving the PTGS-SP and thereby restore the original action of PTGS, resulting in the inhibited growth or reduced toxicity of the virus that has infected organisms. Therefore, the PTGS-SP binding inhibitor of the present invention can be used as an antiviral agent. The antiviral agent of the present invention has a different mechanism of action from that of known antiviral agents and is therefore expected to be sufficiently effective for, for example, viruses resistant to known antiviral agents.

Moreover, the antiviral agent of the present invention inhibits the binding of PTGS-SP to siRNA such that the PTGS-SP function is inhibited. The antiviral agent of the present invention acts on the functions of PTGS-SPs carried in common by many pathogenic viruses and is therefore expected to be effective for a wider range of viruses. Specifically, X-ray crystallography or the like has revealed that many PTGS-SPs bind, at a site called a nucleic acid-binding region, to siRNA (Non-Patent Document 5). It was demonstrated that the PTGS-SPs bind thereto particularly at a site where two or more strongly basic amino acids (arginines or lysines) are consecutive or adjacent in a primary sequence or three-dimensional positional relationship. The presence of the site of PTGS-SP having such strongly basic amino acids with a high frequency is the condition necessary to bind to siRNA and is a common characteristic of the PTGS-SPs carried by pathogenic viruses. Therefore, the antiviral agent of the present invention is expected to be effective for a wide range of viruses.

The antiviral agent of the present invention, when used in animals, produces therapeutic effects on viral diseases caused by pathogenic viruses. Further, the antiviral agent of the present invention, when used in plants, can reduce severe damage caused by viral diseases and significantly improve the commercial value and productivity of crops.

The invention claimed is:

1. A method of inhibiting a PTGS suppressor protein from binding to a substance α, the method comprising:
    administering to an organism in need thereof an effective amount of at least one compound selected from the group consisting of:
    a cyclic ketone compound represented by the following formula (2):

Formula (2)

and
the following reaction products i) and ii):
   i) a reaction product of croconic acid with hydrogen peroxide at a temperature of 20 to 30° C. for 3 days, the reaction product having $^{13C}$-NMR ($D_2O$) spectra of δ 178.6, 129.5, 75.7; and ii) a reaction product of croconic acid with hydrogen peroxide at a temperature of 100° C. for 24 hours, the reaction product having $^{13C}$-NMR ($D_2O$) spectra of δ 195.3, 193.9, 180.5, 178.7, 176.7, 161.7, 151.3, 150.0, 129.7, 75.8, 73.1, 72.5, 59.9, 45.9, 39.8.

2. The method of claim 1, wherein the substance α is siRNA.

3. A method of using a compound as an antiviral agent, the method comprising:

administering to an organism in need thereof an effective amount of at least one compound selected from the group consisting of:

a cyclic ketone compound represented by the following formula (2):

Formula (2)

and the following reaction products i) and ii):

i) a reaction product of croconic acid with hydrogen peroxide at a temperature of 20 to 30° C. for 3 days, the reaction product having $^{13C}$-NMR ($D_2O$) spectra of δ 178.6, 129.5, 75.7; and ii) a reaction product of croconic acid with hydrogen peroxide at a temperature of 100° C. for 24 hours, the reaction product having $^{13C}$-NMR ($D_2O$) spectra of δ 195.3, 193.9, 180.5, 178.7, 176.7, 161.7, 151.3, 150.0, 129.7, 75.8, 73.1, 72.5, 59.9, 45.9, 39.8.

4. The method of claim 3, wherein the compound inhibits binding of a substance α to a PTGS suppressor protein, where substance a has a property of inducing PTGS and a property of binding to the PTGS suppressor protein and shows a decrease in the property of inducing PTGS upon binding to the PTGS suppressor protein.

5. The method of claim 4, wherein the substance α is siRNA.